United States Patent [19]

Mathias et al.

[11] Patent Number: 4,940,796
[45] Date of Patent: Jul. 10, 1990

[54] 2,6-SUBSTITUTED-4-AMINOPYRIDINES AND THEIR CORRESPONDING INTERMEDIATES

[75] Inventors: Lon J. Mathias; Gustavo Cei, both of Hattiesburg, Miss.

[73] Assignee: The University of Southern Mississippi, Hattiesburg, Miss.

[21] Appl. No.: 324,817

[22] Filed: Mar. 17, 1989

[51] Int. Cl.⁵ .................. C07D 471/08; C07D 213/81
[52] U.S. Cl. .................................... 546/323; 540/472; 546/304; 546/309; 546/312
[58] Field of Search .............. 546/304, 309, 310, 312, 546/323; 540/477, 479, 472, 474

[56] References Cited

U.S. PATENT DOCUMENTS 4,661,598  4/1987  Mathias .......................... 546/304

FOREIGN PATENT DOCUMENTS 195413  9/1986  European Pat. Off. ............ 546/312

Primary Examiner—Richard A. Schwartz
Assistant Examiner—Jacqueline Haley
Attorney, Agent, or Firm—Wegner & Bretschneider

[57] ABSTRACT

The present invention is a compound of the formula

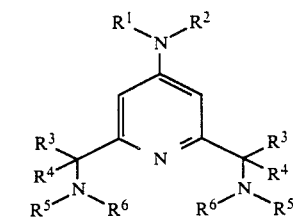

wherein $R^1$ and $R^2$ are independently $C_{1-20}$ alkyl unsubstituted or substituted with a $C_{1-3}$ alcohol, or allyl unsubstituted or substituted with a $C_{1-4}$ alkyl or phenyl, $R_3$ and $R^4$ are independently hydrogen, or $C_{1-20}$ alkyl unsubstituted or substituted with a $C_{1-3}$ alcohol or together $R^3$ and $R^4$ are oxygen, and $R^5$ and $R^6$ are independently $C_{1-20}$ alkyl unsubstituted or substituted with $C_{1-3}$ alcohol or phenyl, hydroxy, $-(CH_2)_{1-3}COOH$, $-CHR^7COOH$ wherein $R^7$ is $C_{1-5}$ alkyl or $C_{1-5}$ alkyl substituted with hydroxy, amino, or carboxy, or allyl unsubstituted or substituted with a $C_{1-4}$ alkyl or phenyl or together $R^5$ and $R^6$ with the two nitrogen atoms form a fused ring having the formula

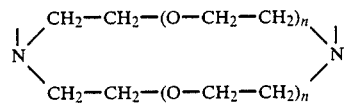

wherein n is 1 or 2, or form a fused ring having the formula

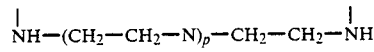

wherein p is an integer from 0 to 3.

6 Claims, No Drawings

2,6-SUBSTITUTED-4-AMINOPYRIDINES AND THEIR CORRESPONDING INTERMEDIATES

The present invention relates to 4-aminopyridines. In particular, it relates to substituted 4-aminopyridines.

4-Dialkylaminopyridines are known as acylation and alkylation catalysts. N,N-dimethylaminopyridine (DMAP) has known metal-binding activity. DMAP residues as pendant groups attached to polymeric backbones are known as more stable metal-binding reagents.

However, more versatile metal-binding aminopyridines had not been developed. In particular, such versatile aminopyridines that can be stabilized by incorporation directly into a polymeric backbone would be advantageous.

Accordingly, the present invention discloses a composition comprising a compound of the formula

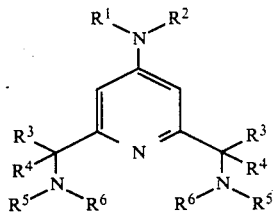

wherein $R^1$ and $R^2$ are independently $C_{1-20}$ alkyl unsubstituted or substituted with a $C_{1-3}$ alcohol, or allyl unsubstituted or substituted with a $C_{1-4}$ alkyl or phenyl, $R^3$ and $R^4$ are independently hydrogen, or $C_{1-20}$ alkyl unsubstituted or substituted with a $C_{1-3}$ alcohol or together $R^3$ and $R^4$ are oxygen, and $R^5$ and $R^6$ are independently $C_{1-20}$ alkyl unsubstituted or substituted with $C_{1-3}$ alcohol or phenyl, hydroxy, —$(CH_2)_{1-3}COOH$, —$CHR^7COOH$ wherein $R^7$ is $C_{1-5}$ alkyl or $C_{1-5}$ alkyl substituted with hydroxy, amino, or carboxy, or allyl unsubstituted or substituted with a $C_{1-4}$ alkyl or phenyl or together $R^5$ and $R^6$ with the two nitrogen atoms form a fused ring having the formula

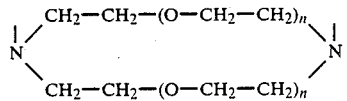

wherein n is 1 or 2, or form a fused ring having the formula

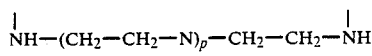

wherein p is an integer from 0 to 3. The present invention is also a polymer made using a compound of the present invention that is polymerizable, an intermediate in making the compound of the present invention, and a method for using the compound and polymer of the present invention. The present invention is useful as a metal complexing agent, for example, for the removal of undesirable metals from waste water by precipitation. Preferably, the groups $R^1$ and $R^2$ are either allyl or methyl, $R^3$ and $R^4$ are each hydrogen or together form an oxygen atom, and $R^5$ and $R^6$ are each methyl. The most preferred compounds are 2,6-bis(N,N-dimethylaminoformyl)-4-diallylamino) pyridine, 2,6-bis(N,N-dimethylaminoformyl)-4-(dimethylamino) pyridine and 2,6-bis(N,N-dimethylaminomethyl)-4-(dimethylamino)pyridine.

Polymerizable compounds of the present invention can be used to make useful polymers as noted above. The polymer of the present invention has repeating units of the formula

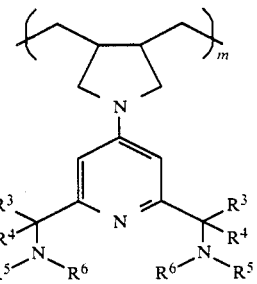

wherein $R^3$, $R^4$, $R^5$, and $R^6$ are as defined hereinabove, and m is an integer from 10–10,000. Preferably $R^3$ and $R^4$ are each hydrogen or together form an oxygen atom, and $R^5$ and $R^6$ are each methyl. Preferably, the variable m is an integer from 10–1,000, more preferably 50–200. Most preferably, the polymer is a 2,6-bis(N,N-dimethylaminoformyl)-4-(diallylamino) pyridine homopolymer or copolymer with diallylamine, diallylamine derivatives such as dimethyldiallylammonium chloride, diallylformamide, and diallylacetamide, acrylates such as methacrylic acid, acrylic acid, and their alkyl esters, and substituted vinyl monomers such as styrene, N-vinylpyrrolidone, vinyl acetate, and vinyl chloride. Polymerization is carried out using well known methods for diallylamine polymerization, such as disclosed in Mathias, et al., *Journal of Applied Polymer Science*, Vol. 33, 1157–1171 (1987).

The intermediate compound of the present invention has the general formula

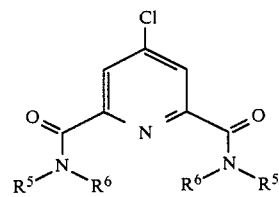

wherein $R^5$ and $R^6$ are as defined hereinabove. The preferred intermediate compound is 2,6-bis(N,N-dimethylaminoformyl)-4-chloropyridine.

The compound of the present invention is preferably made using 2,6-bis(chloroformyl)-4-chloropyridine as a starting material. This compound is well known, and can be made by reacting 3–6 molar equivalents of $PCl_5$ or other chlorine source, such as $POCl_3$ or $SOCl_2$, for 12–72 hours at 0°–150° C. with 4-hydroxypyridine-2,6-dicarboxylic acid (chelidamic acid). An intermediate compound of the present invention is then made by reacting 2,6-bis(chloroformyl)-4-chloropyridine with 2–4 molar equivalents of an amine at −10° to 10° C. for 1–24 hours to produce a 2,6-bis(aminoformyl)-4-chloropyridine. Useful amines include ammonia, amino acids such as glycine, alanine, and leucine and their methyl esters, aminoalcohols such as ethanolamine, 3-aminopropanol, and 4-aminobutanol, diamines or polyamines such as ethanediamine, 1,3-propanediamine, and diethylene triamine .(NH₂C₂H₄NHC₂H₄NH₂), polyaminoethers containing ethylene glycol and diethylene glycol, alkylamines such as dimethylamine and diethylamine, and alkenyl amines such as diallylamine and allylmethylamine. Due to the inherently lower reactivity of the hydroxy group with respect to the amino group, reaction with polyols indicates a higher reaction temperature or longer reaction time. When the amine used is a polyamine, both the polyamine and the intermediate compound are added slowly to a large volume of solvent to favor cyclization with respect to the intermolecular action. Thereafter, the 2,6-bis(aminoformyl)-4-chloropyridine is reacted with a secondary amine to produce a 2,6-bis(aminoformyl)-4-aminopyridine. Useful secondary amines include alkylamines such as dimethylamine, diethylamine, dibutylamine, octylamine, undecylamine, eicosylamine, ethanolamine, and propanol amine.

Another preferred method of making a compound of the present invention eliminates the need to make an intermediate compound. In this process 2,6-bis(chloroformyl)-4-chloropyridine is reacted with a sufficient amine, preferably 3-6 molar equivalents, to replace all of the chlorine atoms in the starting compound and produce directly a 2,6-bis(aminoformyl)-4-aminopyridine.

A further compound of the present invention is made by reacting the 2,6-bis(aminoformyl)-4-aminopyridine with 2-4 molar equivalents of borohydride (BH₃) or other suitable reducing agent, such as lithium aluminum hydride (LiAlH₄) or borohydride complexed with compounds such as triethylamine, for 4-28 hours at 20-50° C. to produce a 2,6-bis (aminomethyl)-4-aminopyridine. Exemplary variations of this preferred compound are made by its reaction with organometallic compounds, such as alkylmagnesium bromide or alkyl lithium, which yields an alkyl group and a hydroxy group at the R³ and R⁴ positions. Further modification can then be effected by elimination of the hydroxy group under strong acidic conditions and hydrogenation with H₂, which yields a hydrogen atom and the alkyl group at the R³ and R⁴ positions (provided the alkyl group has at least one hydrogen atom at position 2). Alternative modification is effected when the hydroxy group is replaced by a bromine atom by reacting the hydroxy derivative with PBr₃, forming an organometallic adduct by reacting the bromine derivative with ether containing magnesium shavings (effecting a Grignard reagent), and then reacting the magnesium adduct with an aldehyde to yield a compound having a 2-hydroxy substituted alkyl group and an alkyl group at the R³ and R⁴ positions.

The polymer of the present invention is made by polymerizing a free radical polymerizable compound of the present invention using well known free radical polymerization techniques in aqueous media. Suitable free radical initiators useful in these known techniques include azo compounds, peroxides, and redox initiators. Preferably, azo initiators are used. Preferably, the amount of initiator used varies between about 0.1 and 10 mole % of the free radical polymerizable compound used, and the reaction proceeds until a polymer having a molecular weight between 3,000 and 60,000 (weight average) is obtained.

The compounds and polymers of the present invention are useful as water treatment chemicals for the removal of metals from water by precipitation. Examples of metals that can be precipitated from aqueous solutions according to the present invention are metals from groups IB, IIB, IIIA and B, IVA and B, VA and B, VIA and B, and VIIB and VIIIB of the Mendeleev periodic table, especially copper (Cu), silver (Ag), zinc (Zn), uranium (U), platinum (Pt), or palladium (Pd). Precipitation is effected by mixing a sufficient amount of the compound or polymer of the present invention with water that contains a salt of the metal of interest.

In order to more clearly describe the present invention, the following non-limiting examples are provided. In the examples, all parts and percentages are by weight unless indicated otherwise.

EXAMPLE 1

Synthesis of 2,6-bis(chloroformyl)-4-chloropyridine (2)

Chelidamic acid (4-hydroxypyridine-2,6-dicarboxylic acid), (35.15 g, 0.192 mol) was suspended in 300 ml dry chloroform (CHCl₃) in a 1 liter three-neck flask provided with Graham condenser, CaCl₂-moisture trap and magnetic stirrer. The mixture was cooled to 0° C. in an ice bath and PCl₅ (140 g, 0.67 mol) was added in a 10 min. period. Gentle bubbling and HCl evolution through the moisture trap was observed after addition of all PCl₅. The light brown suspension was left overnight at 0° C. It was then heated to reflux during 72 hrs and a dark brown solution was obtained. The reaction flask was cooled to 0° C. and the contents slowly poured into one liter of an ice-water mixture. Care was taken to avoid a too-fast addition leading to local temperature increases, which would have caused some hydrolysis of the product along with that of PCl₅. Therefore the temperature was maintained below 10° C. The two-phase mixture was poured into a separation funnel. Some formation of the partially hydrolyzed diacid 1 was observed as a brown precipitate, which settled between the two phases in the separation funnel. The chloroform phase containing 2 was separated and filtered through phase separation filter paper to remove most of the water. More chloroform was added to speed up the separation of both phases, which sometimes tended to form emulsions. While maintaining a temperature below 10° C., both phases were separated and the organic phase filtered again, this time with phase separation paper. The organic solution was then treated with anhydrous CaCl₂. After filtration, this was rotary evaporated and the dark brown product obtained sublimed in an oil bath at 120° C. under a vacuum of 5 mm Hg. The sublimation was repeated and yielded 2 as long white needles of melting point 98-100° C. The product was then stored under anhydrous conditions. The reaction is represented schematically below.

Alternative synthesis of 2:

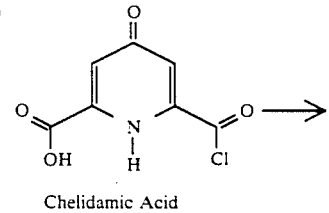

Chelidamic Acid

-continued

Alternative synthesis of 2:

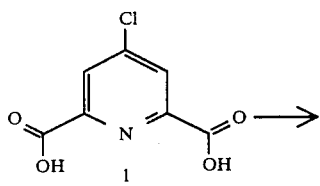

Chelidamic acid was reacted with PCl₅ as described above. After pouring into ice water mixture, hydrolysis to 4-chloro-2,6-pyridine dicarboxylic acid 1 occurred after the mixture was permitted to reach room temperature. The brown precipitate formed was filtered and dried under vacuum. It was then refluxed in excess SOCl₂ overnight. Thionyl chloride was removed by vacuum distillation. The crude acyl chloride 2 was recrystallized in CHCl₃-petroleum ether and purified by sublimation as described above. The reaction is represented schematically below.

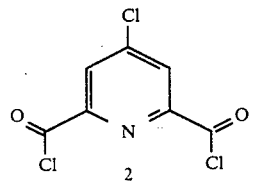

Synthesis of 2,6-bis(dimethylformamino)-4-chloropyridine (3)

2,6-Bis(chloroformyl)-4-chloropyridine (2) (23.5 g, 0.1 mol) was dissolved in dry dimethylformamide (72 g) in a three-neck flask (500 ml) provided with thermometer, magnetic stirrer and addition funnel with pressure compensation. The mixture was cooled to 0° C. and a solution of dimethylamine (27 g) in dry dimethylformamide (75 g) was added through the addition funnel. After complete addition, the funnel was replaced by a Liebig condenser and the mixture heated 2 hrs at 80° C. A vacuum distillation head was attached and most of the dimethylformamide distilled. Aqueous KOH was added to the remaining product to raise the pH to 11. This was then extracted with CHCl₃, filtered with phase separation paper, and rotary evaporated. The resulting white crystals were 99% pure (as determined by comparing peak areas of a gas chromatograph of a chloroform solution using a fused silica megabore column with 5% phenyl-methyl polysiloxane and flame ionization detector) with a melting point of 138–140° C. The yield was approximately 40%. The reaction is represented schematically below.

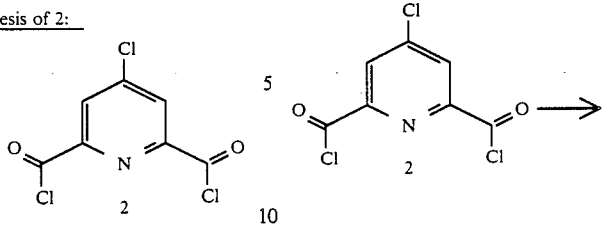

EXAMPLE 2

Synthesis of the monomer 2,6-Bis(N,N-dimethylaminoformyl)-4-(diallylamino)-pyridine (4)

2,6-Bis(dimethylformamino)-4-chloropyridine (3) (8.7 g, 0.039 mol) was refluxed with freshly distilled diallylamine (30 ml) in a three-neck flask (100 ml) provided with Liebig condenser with N₂ inlet, thermometer and magnetic stir bar. After 72 hrs, 98% conversion was achieved (followed by GC) and the reflux (110° C.) was stopped. The reaction mixture was shaken with excess 10% NaOH and extracted with CHCl₃. The organic phase was then filtered with phase separation filter paper and rotary evaporated. Distillation under vacuum yielded a product still contaminated with diallylamine. A 95% pure product was obtained by recrystalization from ethyl acetate - cyclohexane (50/50). Higher purity was obtained using column chromatography on silica gel. First, unreacted 3 was eluted with ethyl acetate. The compound 4 was eluted with methanol and, after concentration, was 99% pure by gas chromatography (GC), determined as in EXAMPLE 1. The reaction is represented schematically below.

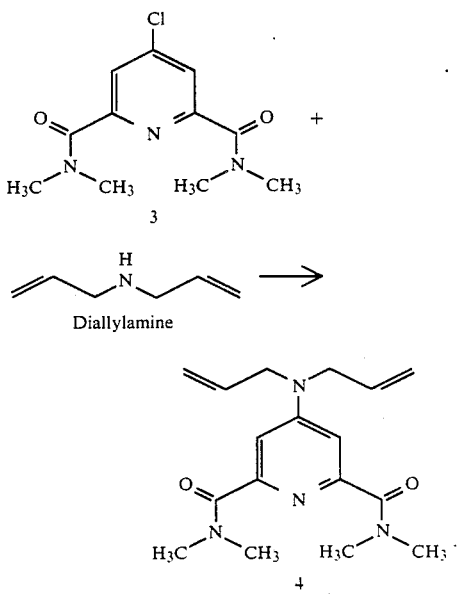

EXAMPLE 3

Polymerization of the monomer
2,6-Bis(N,N-dimethylaminoformyl)-4-(diallylamino)-pyridine (4)

2,6-Bis(N,N-dimethylaminoformyl)-4-(diallylamino)-pyridine (4) (1.72 g, $5.5 \times 10^{-3}$ mol), 5 ml $H_2O$, 0.7 ml conc. HCl and 2,2'-azobis(2-amidinopropane) hydrochloride catalyst (V50, Wako Chemicals USA) (0.015 g, $5.5 \times 10^{-5}$ mol) were charged into a 50 ml Schlenk flask. The solution was submitted to three freeze-thaw cycles and immersed in a water bath at 60° C. Additional catalyst (0.24 g) was added after 30 hours. Precipitation of a pale yellow solid was observed after two days. Polymerization was stopped after five days. The precipitate was filtered, washed with water, and the wash water was combined with the yellow supernatant liquid, which was enclosed in cellulose dialysis membranes having a pore size sufficient to filter polymers having a molecular weight greater than 3,000–6,000 weight average molecular weight, i.e., they have a molecular weigh cut-off of 3,000–6,000. The bags were then immersed in fresh water for three days, after which the bag contents were freeze dried. The freeze-died polymer was a yellow-orange powder, very soluble in water and methanol, but insoluble in THF(tetrahydrofurane) or $CHCl_3$. The reaction is represented schematically below.

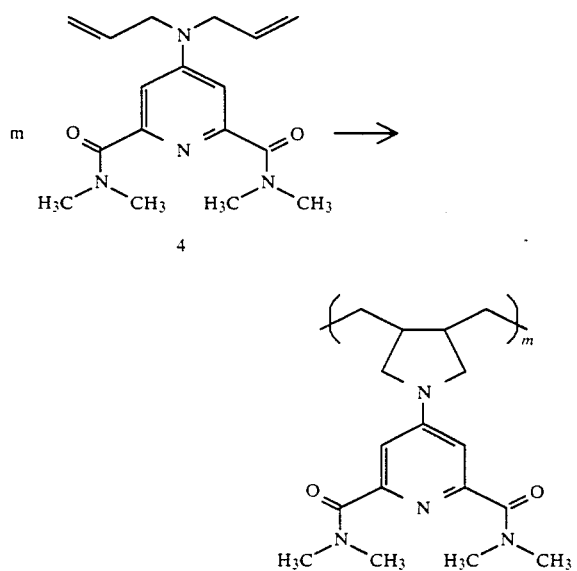

Chelating activity of the homopolymer of 4 Chelating activity of the homopolymer of 2,6-bis(dimethylformamido)-4-diallylamino-pyridine (4) with cupric salts was demonstrated to show that the homopolymer is useful in removing metals from water by precipitation. A $^{13}C$ NMR spectrum (number of scans: 2254) of the polymer was taken. A concentrated $Cu(NO_3)_2$ solution was added to the polymer at a 0.2 metal/polymer ratio, which led to instantaneous precipitation of a green product, which was redissolved in excess polymer. Comparison of a $^{13}C$ NMR spectrum (number of scans: 1217) taken after addition of the metal salt with the spectrum of the polymer before addition of the metal salt showed decrease of intensity of the absorption peaks of the 3-pyridine carbons at 105 ppm and the carbonyl carbons at 177 ppm, which indicated complexing with the metal. All spectra were recorded on a Bruker MSL-200 instrument at room temperature with TMS (tetramethylsilane) as chemical shift standard.

EXAMPLE 4

Copolymerization of the monomer 4 (1.00 g, $3.20 \times 10^{-3}$ mol) with diallylamine (1.00 g, $1.03 \times 10^{-2}$ mol) was carried out under the same conditions as in EXAMPLE 3, except that no additional catalyst was added after 30 hours and polymerization was stopped after 72 hours. Filtering and dialysis was carried out as in EXAMPLE 3. The freeze dried product was a white-yellow glassy material, which was soluble in water and methanol, but insoluble in THF an chloroform. The presence of pyridine rings in the final product was determined by $^{13}C$-NMR spectroscopy.

EXAMPLE 5

Synthesis of
2,6-bis(N,N-dimethylaminoformyl)-4-(dimethylamino)-pyridine (5)

2,6-Bis(chloroformyl)-4-chloropyridine (2) (5 g, 0.06 mol) was dissolved in dry dimethylformamide (60 ml) in a three-neck flask (500 ml) provided with thermometer, magnetic stirrer and addition funnel. A solution of dimethylamine (29 g) in dry dimethylformamide (72 g) was added slowly under stirring through the addition funnel. The flask was kept at room temperature for 6 hours and then heated 6 hours at 80° C. Stirring at room temperature was continued overnight. Dimethylformamide was then distilled off under vacuum. The yellow product remaining in the flask was dissolved in 200 ml NaOH 10% and extracted with four portions of $CHCl_3$ (50 ml each). After filtration with phase separation filter paper the solvent was rotary evaporated. Recrystalization in $CHCl_3$-cyclohexane yields white crystals of melting point 175–178° C. The reaction is represented schematically below.

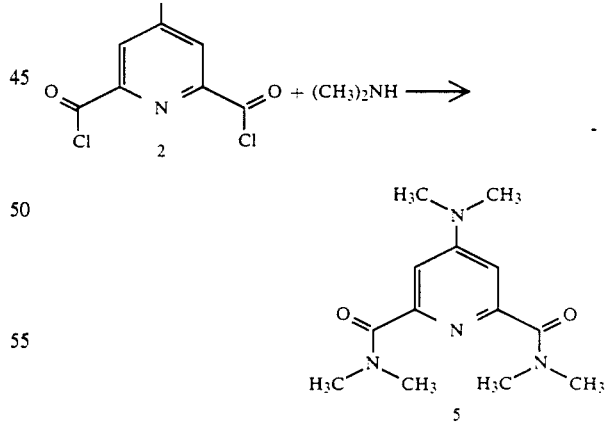

Chelating activity of the compound 5

All spectra were recorded on a Bruker MSL-200 instrument at room temperature with TMS (tetramethylsilane) as chemical shift standard. A $^{13}C$-NMR spectrum (number of scans: 2034) of compound 5 in water was taken. After addition to the compound of a manganese salt ($MnCl_2.4H_2O$) at a metal/ligand ratio of 0.0032 a second $^{13}C$-NMR spectrum (number of scans: 1536) was made. The peak corresponding to the carbonyl carbon in the first spectrum disappears in the second, while the other peaks experience only slight broadening. The largest distortion of the spectrum was expected in the absorption of those nuclei closest to th complexed metal ion. The vanishing of the carbonyl carbon signal indicated that complexation had taken place in that proximity. This demonstrated that the compound is useful in removing metals from water by precipitation.

EXAMPLE 6.

Synthesis of 2,6-Bis(N,N-dimethylaminomethyl)-4-(dimethylamino)-pyridine (6)

A three-neck flask (500 ml) provided with dropping funnel, reflux condenser and magnetic stir bar was dried at 100° C. and allowed to cool to room temperature in a dry $N_2$ atmosphere. 2,6-bis(N,N-dimethlaminoformyl)-4-(dimethylamino) pyridine (5) (5 g, 0.019 mol) was suspended in dry THF (20 ml) and cooled to 0° C. $BH_3$-THF solution (120 g, 0.08 mol $BH_3$) was transferred by means of a hypodermic syring into the dropping funnel. The solution was then added in a 20 min. period under stirring and cooling. After 2 hours the white suspension was refluxed for 48 hours during which it turned into a pale green solution. 6M HCl (200 ml) was then added at 0° C. under stirring whereby $H_2$ gas evolves. THF was distilled at atmospheric pressure; the amine-borane complex was then destroyed (further $H_2$ evolution). After leaving overnight at room temperature, NaOH pellets were slowly added under cooling and stirring until pH 11 was reached. The solution was transferred to a separation funnel (some $H_2O$ had to be added to redissolve NaCl) and extracted with $CH_2Cl_2$. The organic phase was filtered through phase separation filter paper and rotary evaporated. The final solvent removal in high vacuum yielded 2.2 g of a greenish white, slightly fishy smelling syrup that solidified in the refrigerator. The product was 99% pure by GC and its structure was confirmed by $^1H$ and $^{13}C$-NMR spectroscopy and elementary analysis.

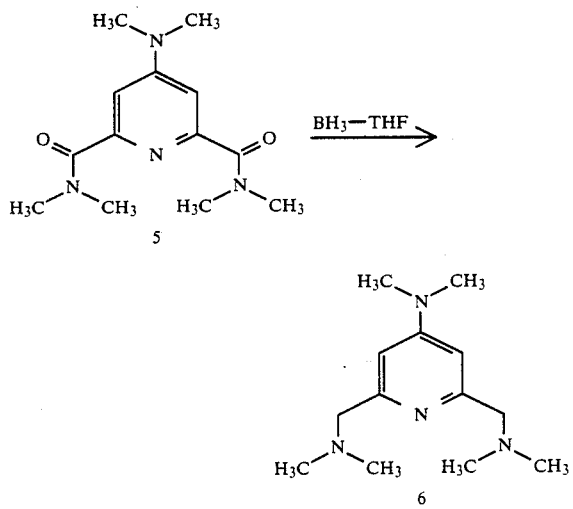

We claim:
1. A compound of the formula

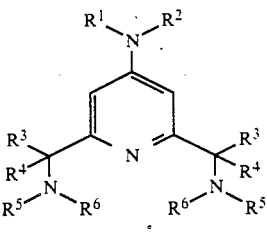

wherein (a) $R^1$ and $R^2$ are independently (i) $C_{1-20}$ alkyl unsubstituted or substituted with a $C_{1-3}$ alcohol, or (ii) allyl unsubstituted or substituted with a $C_{1-4}$ alkyl or phenyl, (b) $R^3$ and $R^4$ are independently (i) hydrogen, or (ii) $C_{1-20}$ alkyl unsubstituted or substituted with a $C_{1-3}$ alcohol or (iii) together $R^3$ and $R^4$ are oxygen, and (c) $R^5$ and $R^6$ are independently (i) $C_{1-20}$ alkyl unsubstituted or substituted with $C_{1-3}$ alcohol or phenyl, (ii) hydroxy, (iii) $-(CH_2)_{1-3}COOH$, (iv) $-CHR^7COOH$ wherein $R^7$ is $C_{1-5}$ alkyl or $C_{1-5}$ alkyl substituted with hydroxy, amino, or carboxy, or (V) allyl unsubstituted or substituted with a $C_{1-4}$ alkyl or phenyl or (vi) together $R^5$ and $R^6$ with the two nitrogen atoms form a fused ring having the formula

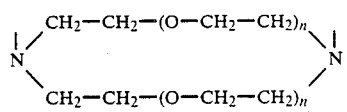

wherein n is 1 or 2, or form a fused ring having the formula

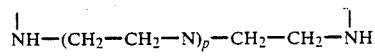

wherein p is an integer from 0 to 3.
2. The compound of claim 1 wherein $R^1$ and $R^2$ are each allyl or $C_1$-$C_4$ alkyl.
3. The compound of claim 1 wherein $R^3$ and $R^4$ are each hydrogen or together oxygen.
4. The compound of claim 1 wherein $R^5$ and $R^6$ are each $C_1$-$C_4$ alkyl.
5. A compound of the formula

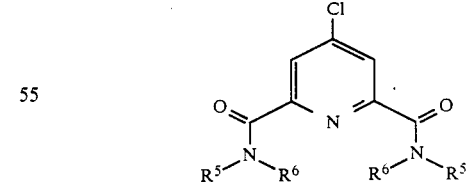

wherein $R^5$ and $R^6$ are independently $C_{1-20}$ alkyl unsubstituted or substituted with $C_{1-3}$ alcohol or phenyl, hydroxy, $-(CH_2)_{1-3}COOH$, $-CHR^7COOH$ wherein $R^7$ is $C_{1-5}$ alkyl or $C_{1-5}$ alkyl substituted with hydroxy, amino, or carboxy, or allyl unsubstituted or substituted with a $C_{1-4}$ alkyl or phenyl or together $R^5$ and $R^6$ with the two nitrogen atoms form a fused ring having the formula

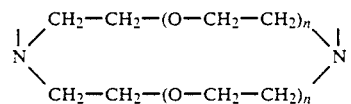
wherein n is 1 or 2, or form a fused ring having the formula
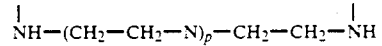
wherein p is an integer from 0 to 3.
6. The compound of claim 5 wherein $R^5$ and $R^6$ are independently $C_1$-$C_4$ alkyl.
* * * * *